United States Patent [19]

Aumüller et al.

[11] Patent Number: 5,728,888
[45] Date of Patent: Mar. 17, 1998

[54] PREPARATION OF HYDROXYLATED BENZOPHENONES

[75] Inventors: Alexander Aumüller, Neustadt; Gunter Brill, Hassloch; Peter Böttcher, Carlsberg, all of Germany

[73] Assignee: BASF Aktiengesellschaft, Ludwigshafen, Germany

[21] Appl. No.: 806,257

[22] Filed: Feb. 21, 1997

[30] Foreign Application Priority Data

Mar. 1, 1996 [DE] Germany ............... 196 07 809.1

[51] Int. Cl.⁶ .................................................. C07C 45/65
[52] U.S. Cl. .................................................. 568/315
[58] Field of Search .................................................. 568/315

[56] References Cited

U.S. PATENT DOCUMENTS 2,694,729  11/1954  Wynn et al. .
2,861,105  11/1958  Stanley .

FOREIGN PATENT DOCUMENTS 41 34 773  11/1992  Germany .

OTHER PUBLICATIONS

CA 93: 26183. Abs from Indian J. Chem 1979, 17B(4) 382–4–"Part I Synthesis of Basic Ethers from phenolic 2-aroyl-3-phenyl Benzofurans".
CA 101: 54714 Abst from JP58216139 –1982 Hydroxybenzophenones.
Database WPI, Derwent Publications, JP 5 8216–139, Dec. 15, 1983.

Primary Examiner—C. Warren Ivy
Assistant Examiner—Jean F. Vollano
Attorney, Agent, or Firm—Oblon, Spivak, McClelland, Maier & Neustadt, P.C.

[57] ABSTRACT

Hydroxylated benzophenonens are prepared from completely or partially methylated hydroxybenzophenones by reacting these methyl ethers with $AlCl_3$ and subsequently hydrolyzing with water, the reaction being carried out in the presence of one or more compounds from the class of ureas or carboxamides.

9 Claims, No Drawings

PREPARATION OF HYDROXYLATED BENZOPHENONES

The present invention relates to a process for preparing hydroxylated benzophenones from completely or partially methylated hydroxybenzophenones by reaction of these methyl ethers with $AlCl_3$ and subsequent hydrolysis with water.

Elimination of the methyl groups from methylated hydroxybenzophenones is a reaction which has been known for a long time. This ether cleavage can be catalyzed by various acids, eg. by the Lewis acid $AlCl_3$. Thus, U.S. Pat. No. 2,694,729 describes the conversion of 2,2',4,4'-tetramethoxybenzophenone into 2,2',4,4'-tetrahydroxybenzophenone in the presence of $AlCl_3$ and chlorinated hydrocarbons. JP-A 58 216 139 describes the same reaction in the presence of $AlCl_3$ and o-dichlorobenzene. In turn, DE-C1-41 34 773 describes this reaction in the presence of $AlCl_3$ and aromatic hydrocarbons, especially xylene.

However, the yields are unsatisfactory in the known demethylation processes. The reason for the unsatisfactory yields is usually agglomeration of the $AlCl_3$ with the precursors and, as a consequence of these agglomerations, impairment of the stirrability of the reaction mixture.

It is an object of the present invention to find a process for the demethylation of methylated hydroxybenzophenones which avoids these agglomerations and provides the hydroxybenzophenones in good yields.

We have found that this object is achieved by a process for preparing hydroxylated benzophenones from completely or partially methylated hydroxybenzophenones by reaction of these methyl ethers with $AlCl_3$ and subsequent hydrolysis with water, wherein the reaction with $AlCl_3$ is carried out in the presence of one or more compounds from the class of ureas or carboxamides.

The compounds from the class of ureas or carboxamides can be varied within wide limits. As a rule, urea derivatives or carboxamides which can be obtained as easily and cheaply as possible will be used. Hence examples of suitable compounds are those of the general formula I

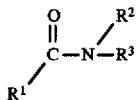

where the variables have the following meanings:

$R^1$ hydrogen, $C_1$–$C_4$-alkyl, amino, di-$C_1$–$C_4$-alkylamino, $C_1$–$C_4$-monoalkylamino, phenylamino, diphenylamino, piperidinyl or pyrrolidinyl and $R^2$, $R^3$ hydrogen, $C_1$–$C_4$-alkyl, phenyl or $C_5$- or $C_6$-cycloalkyl or, together with the nitrogen atom to which they are bonded, a piperidinyl or pyrrolidinyl radical.

Examples of compounds of the general formula I are urea compounds such as N,N'-dimethylurea, N-methylurea, tetramethylurea, N,N'-dimethylethyleneurea, N,N'-dimethylpropyleneurea, phenylurea, N,N'-diphenylurea and, particularly preferably for reasons of cost, unsubstituted urea.

Examples of suitable carboxamides of the general formula I are formamide, dimethylformamide, acetamide, dimethylacetamide, propionamide, caprolactam and N-methylpyrrolidone, particularly preferably dimethylformamide of these.

Various singly or multiply methoxylated benzophenones can be reacted by the process according to the invention. In this connection, ether cleavage in the 2 and 2' positions can be achieved particularly easily, which makes partial hydrolysis to mixed hydroxylated/methoxylated benzophenones possible. The reaction conditions, especially the reaction time and temperature, for this partial hydrolysis, are advantageously determined in a known manner in each particular case.

The process according to the invention provides an advantageous route to 2,2',4,4'-tetrahydroxybenzophenone, a product which has a wide variety of possible uses, eg. as UV absorber. The starting point in this case is preferably 2,2',4,4'-tetramethoxybenzophenone. This precursor may also contain up to 50% of 2-hydroxy-2',4,4'-trimethoxybenzophenone. Tetrahydroxybenzophenone can also be obtained from 2,2'-dihydroxy-4,4'-dimethoxybenzophenone.

The molar ratio of $AlCl_3$ to the completely or partially methylated hydroxybenzophenone can be varied in the process according to the invention. However, it has been found that a large excess of $AlCl_3$ often results in particularly good yields. This excess can in fact preferably be chosen to be so large that the reaction is virtually carried out in an $AlCl_3$ melt. The abovementioned molar ratio is preferably from 5 to 30, particularly preferably from 10 to 20. A smaller molar ratio, eg. from 1.5 to 3, may also be sufficient for benzophenones with few methoxy substituents, eg. one or two.

According to the invention, a compound from the class of ureas or carboxamides is added to the mixture. The molar ratio of $AlCl_3$ to these compounds is chosen so that the mixture remains satisfactorily stirrable and substantially homogeneous at the reaction temperature. In general, this is achieved by a molar ratio of from 0.5 to 20, preferably by a molar ratio of from 1 to 10.

The preferred reaction temperature depends on the $AlCl_3$/urea or carboxamide compound molar ratio and on the required product. The temperature for partial methylation is preferably relative low and for complete methylation is usually somewhat higher. The temperature is generally from room temperature (20° C.) to 160° C., preferably from 30° to 80° C., particularly preferably from 40° to 60° C.

The reaction is preferably carried out by first mixing $AlCl_3$ and the urea or carboxamide compound at 100° to 160° C., preferably at 140° to 160° C. The mixture is then cooled to 20°–50° C., the precursor is stirred in and then the reaction is carried out at 40°–60° C.

The pressure is not a critical parameter for the reaction. In general, the reaction is carried out under atmospheric pressure, but elevated pressure may be advantageous, for example when volatile carboxamides are used.

After the reaction with $AlCl_3$, the reaction mixture is hydrolyzed in a conventional way by adding water. It is advantageous to add active carbon to the hydrolysis mixture in order, for example, to bind thermal condensation products.

The workup of the hydroxybenzophenones from the mixture takes place in a conventional way, for example by filtration, acidification, filtration of the precipitated part with suction, washing and drying.

In the process according to the invention hydroxybenzophenones are obtained in high purity (often over 99%) and in good yield (often over 90% of theory).

The hydroxybenzophenones prepared according to the invention are preferably used as UV absorbers, eg. for plastics and paints, or as precursors for such UV absorbers. Because of their high purity, they are particularly suitable as UV absorbers in cosmetics such as ointments, oils, lotions, sunscreen agents and tablets, perfumes, shaving lotions etc.

EXAMPLES

Example 1

(Comparative Example)

Preparation of 2,2',4,4'-tetrahydroxybenzophenone as disclosed in JP-A-58 216 139

A mixture of 300 ml of o-dichlorobenzene, 117.4 g (0.88 mol) of $AlCl_3$ and 60.5 g (0.20 mol) of 2,2',4,4'-tetramethoxybenzophenone was heated to 115° C. Above only 70° C. a solid composition deposited on top of the solvent, and the mixture was no longer stirrable. After 3.5 hours, the o-dichlorobenzene was decanted off, the solid residue was mechanically comminuted and added together with the solvent to 1 l of water. After stirring at 25° C. for 3 hours, the precipitate was filtered off with suction, washed with water and dried at 125° C. under reduced pressure.

Yield: 44.5 g of crude product

Melting point: 193°–198° C.

Recrystallization from water resulted in 37.2 g of product.

Melting point: 195°–199° C.

Purity (HPLC): 97.2%.

Example 2

Preparation of 2,2',4,4'-tetrahydroxybenzophenone 440 g (3.30 mol) of $AlCl_3$ were stirred into 120 g (1.64 mol) of dimethylformamide in such a way that the temperature remained below 160° C. After cooling to 30° C., 60.5 g (0.20 mol) of 2,2',4,4'-tetramethoxybenzophenone were introduced into the mixture, which was easily stirrable. The mixture was stirred at about 50°–52° C. for 4.5 hours and then added to 1.8 l of water to which 3 g of active carbon had been added. The hydrolyzate was filtered at about 95° C., and then 65 g of concentrated hydrochloric acid were added to the filtrate. The precipitate was filtered off with suction at 25° C., washed with water and dried at 125° C. under reduced pressure.

Yield: 45.5 g

Melting point: 198°–200° C.

Purity (HPLC): 99.2%.

Example 3

Preparation of 2,2',4,4'-tetrahydroxybenzophenone 82.2 g (0.30 mol) of 2,2'-dihydroxy-4,4'-dimethoxybenzophenone were reacted with 600 g of $AlCl_3$ (4.50 mol) and 180 g (2.47 mol) of DMF (dimethylformamide) as in Example 2, and the product was worked up as described.

Yield: 68.0 g

Melting point: 198°–200° C.

Purity (HPLC): 99.5%

Example 4

Preparation of 2,2',4,4'-tetrahydroxybenzophenone in the presence of urea 54.8 g of 2,2'-dihydroxy-4,4'-dimethoxybenzophenone (0.20 mol) were reacted with 400 g of $AlCl_3$ (3.0 mol) and 120 g (2.0 mol) of urea as in Example 3, and the product was worked up as described.

Yield: 40.3 g

Melting point: 198°–200° C.

Purity (HPLC): 99.3%

We claim:

1. A process for preparing hydroxylated benzophenones from completely or partially methylated hydroxybenzophenones by reaction of these methyl ethers with $AlCl_3$ and subsequent hydrolysis with water, wherein the reaction with $AlCl_3$ is carried out in the presence of one or more compounds from the class of ureas or carboxamides.

2. A process as claimed in claim 1, wherein dimethylformamide is employed as carboxamide.

3. A process as claimed in claim 1, wherein the reaction is carried out in the presence of urea.

4. A process as claimed in any of claims 1 to 3 for preparing 2,2',4,4'-tetrahydroxybenzophenone.

5. A process as claimed in claim 1, wherein the molar ratio of $AlCl_3$ to the completely or partially methylated hydroxybenzophenone is from 5 to 30.

6. A process as claimed in claim 5, wherein the molar ratio of $AlCl_3$ to the completely or partially methylated hydroxybenzophenone is from 10 to 20.

7. A process as claimed in claim 1, wherein the molar ratio of $AlCl_3$ to the compound from the class of ureas or carboxamides is from 0.5 to 20.

8. A process as claimed in claim 7, wherein the molar ratio of $AlCl_3$ to the compound from the class of ureas or carboxamides is from 1 to 10.

9. A process as claimed in claim 1, wherein the reaction is carried out at from 30° to 80° C.

* * * * *